United States Patent
Fishbein et al.

[11] Patent Number: 5,976,144
[45] Date of Patent: Nov. 2, 1999

[54] HOLLOW DOME REAMER WITH REMOVABLE TEETH

[75] Inventors: Meyer Fishbein, Rancho Mirage, Calif.; Patrick M. White, Mahwah, N.J.

[73] Assignee: Vozeh Equipment Corp., Franklin Lakes, N.J.

[21] Appl. No.: 09/040,861

[22] Filed: Mar. 18, 1998

[51] Int. Cl.$^6$ .................................................. A61B 17/00
[52] U.S. Cl. ................................ 606/80; 606/70; 606/81; 606/82; 623/20; 623/22
[58] Field of Search .................................. 606/80, 70, 81, 606/100, 96, 180, 82–88; 623/20–22; 908/24; D24/8; D8/8

[56] References Cited

U.S. PATENT DOCUMENTS

| | | |
|---|---|---|
| D. 248,967 | 8/1978 | Shea et al. . |
| D. 258,237 | 2/1981 | Anspach . |
| D. 262,823 | 1/1982 | House, II . |
| D. 262,849 | 2/1982 | Schoenig . |
| D. 272,648 | 2/1984 | Bolesky et al. . |
| D. 273,806 | 5/1984 | Bolesky et al. . |
| 3,630,204 | 12/1971 | Fishbein . |
| 3,633,583 | 1/1972 | Fishbein . |
| 3,702,611 | 11/1972 | Fishbein . |
| 3,943,916 | 3/1976 | Vadas . |
| 4,004,581 | 1/1977 | Heimke et al. . |
| 4,023,572 | 5/1977 | Weigand et al. . |
| 4,116,200 | 9/1978 | Braun et al. . |
| 4,131,116 | 12/1978 | Hedrick . |
| 4,271,849 | 6/1981 | Rehder . |
| 4,273,117 | 6/1981 | Neuhauser . |
| 4,473,070 | 9/1984 | Matthews et al. . |
| 4,611,587 | 9/1986 | Powlan . |
| 4,621,637 | 11/1986 | Fishbein . |
| 4,712,951 | 12/1987 | Brown . |
| 4,811,632 | 3/1989 | Salyer . |
| 4,946,461 | 8/1990 | Fischer . |
| 5,100,267 | 3/1992 | Salyer . |
| 5,116,165 | 5/1992 | Salyer . |
| 5,171,312 | 12/1992 | Salyer . |
| 5,171,313 | 12/1992 | Salyer . |
| 5,203,653 | 4/1993 | Kudla . |
| 5,236,433 | 8/1993 | Salyer . |
| 5,282,804 | 2/1994 | Salyer . |
| 5,295,992 | 3/1994 | Cameron . |
| 5,299,893 | 4/1994 | Salyer et al. . |
| 5,376,092 | 12/1994 | Hein et al. . |
| 5,501,686 | 3/1996 | Salyer . |

*Primary Examiner*—Michael Buiz
*Assistant Examiner*—Lien Ngo
*Attorney, Agent, or Firm*—Fulwider Patton Lee & Utecht, LLP

[57] ABSTRACT

The surgical reamer has a hollow dome with apertures spaced apart arranged in arcs extending from an apex of the dome to the base portion of the dome, and removable teeth positioned in the apertures. Each cutting tooth has a flange that is aligned flush with the external surface of the dome, and a raised cutting edge extending above the flange and the external surface of the dome, and an interior passageway communicating between the outside and inside of the dome. In one embodiment, a base plate is removably secured on the base portion of the dome to provide closure of the central cavity of the dome.

31 Claims, 10 Drawing Sheets

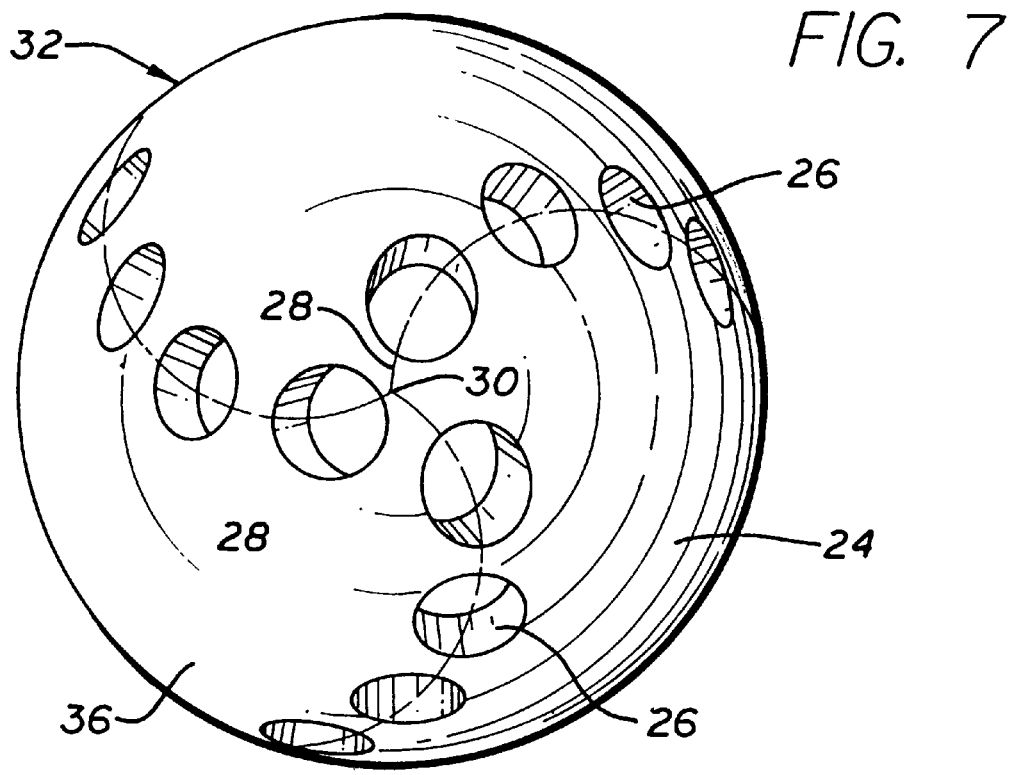
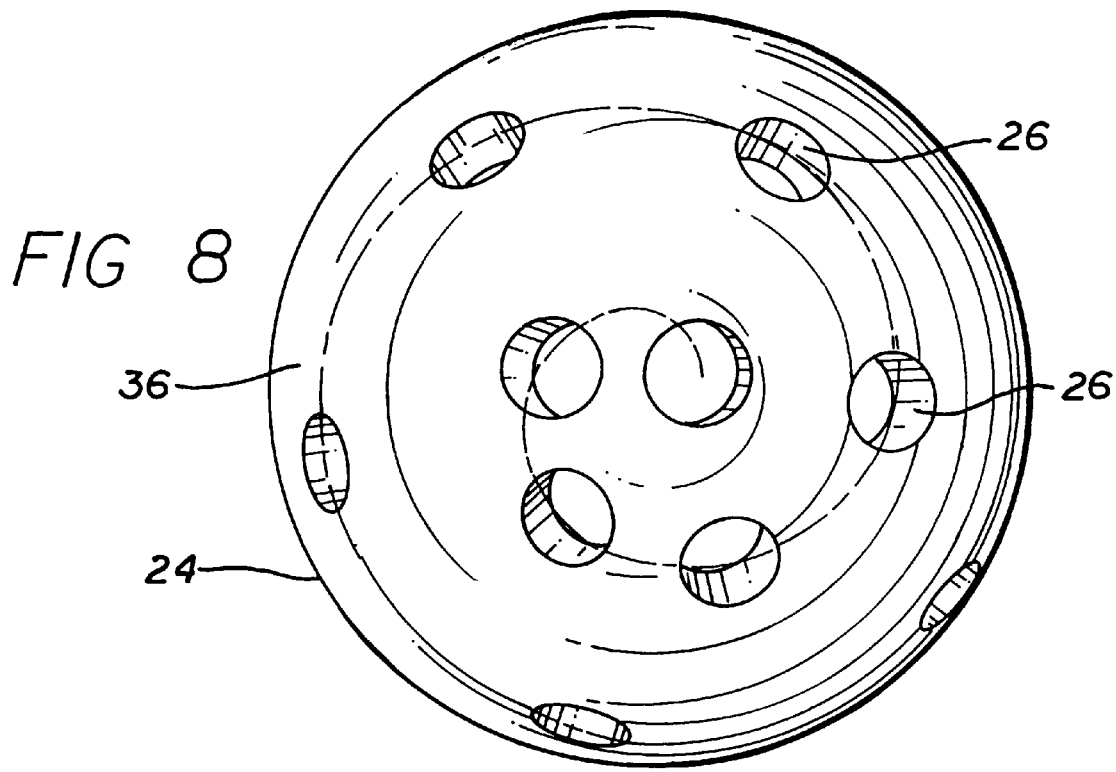

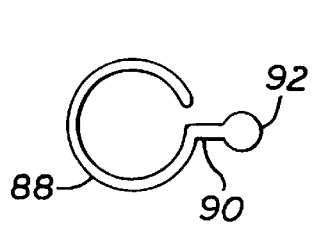
FIG. 19
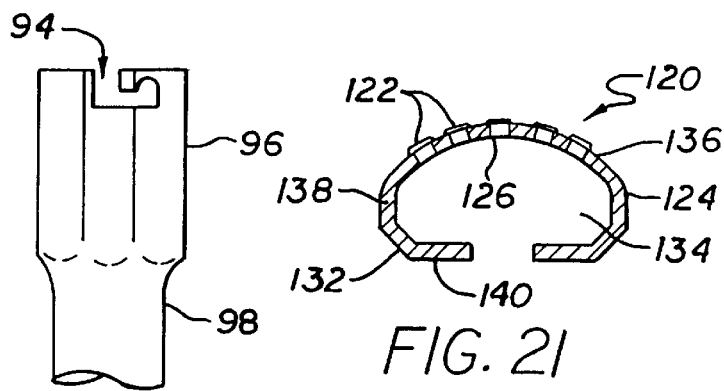
FIG. 20
FIG. 21
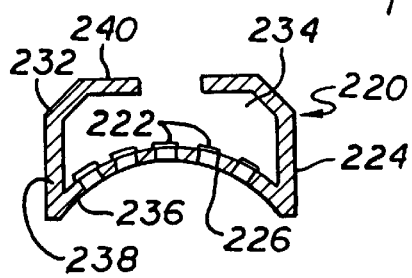
FIG. 22
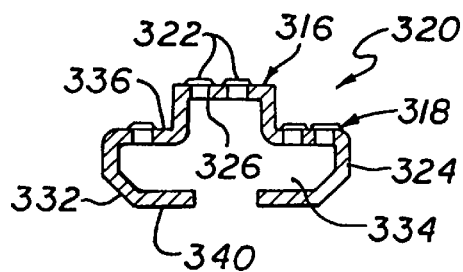
FIG. 23
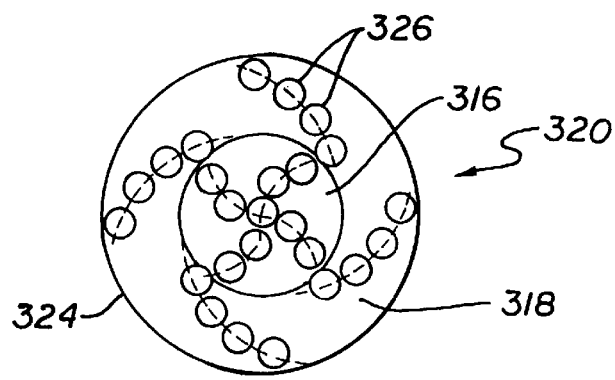
FIG. 24

HOLLOW DOME REAMER WITH REMOVABLE TEETH

BACKGROUND OF THE INVENTION

1. Field of the Invention

This invention relates generally to surgical devices, and more particularly concerns a rotatable surgical cutting tool for shaping a joint socket in preparation for receiving a joint prosthetic device.

2. Description of Related Art

It is now common practice in the treatment of severe cases of arthritic and other forms of degenerative joint diseases, especially the hip, to shape the hip joint socket by removing diseased and eroded bone and cartilage to conform with the shape of a prosthetic device to be implanted. Prior to installing a hip joint prosthesis, for example, articular cartilage and bone is commonly removed from the socket to reshape the acetabulum to accurately match the dimensions of the prosthetic device to be implanted. In the past, the tissue and debris removed from the hip socket was discarded; however, more recently, it has become important to capture the debris for preservation and use later in the procedure.

It is generally desirable for milling devices and reamers used in preparing a joint socket for a prosthesis to have cutting edges that can cut through a wide variety of tissue, such as joint cartilage and bone tissue, ranging in density from the soft or porous tissue to the denser bone. The surgical tools with hollow cutting heads are more widely used than other more open designs, because hollow head devices allow tissue and other debris to be captured within the cutting head.

Two distinct types of hollow dome cutting tools are currently available that capture the debris. One type employs a slotted dome with adjacent blades that are shaped to generate a socket, when rotated, conforming to the shape and dimensions of the prosthesis to be implanted. The debris cut by the blades falls through slots in the dome.

In another type of surgical milling tool, commonly called a "grater" reamer, the milling cutters are formed on the body by upsetting the body around openings in the body, and sharpening selected edges of the upset portions of the body. The surgical milling tool has a body with a hemispherically-shaped outer surface, an internal cavity, and milling cutters formed out of the perforations in the body at spaced-apart locations on the outer surface. The tool can be rotated in a joint socket to mill the tissues of the joint socket, such as for preparation of the joint socket for a prosthesis. The perforations in the body communicate with the internal cavity which receives the debris. The milling cutters of the milling tool are formed as cup-shaped projections extending above the perforations that face in a direction of rotation, and are arranged in a series of arcs extending circumferentially around the body. The outer wall of the milling tool forming the cup-shaped cutting edge projections is relatively thin, resulting in reduced cutting accuracy. The milling tool and cutting edge projections are formed of sheet steel, which can become dull relatively rapidly during use. Typically, if the cutting surfaces are formed integrally with the shell, such as with raised cutting edges formed directly in the shell, the manufacturing of the devices becomes very costly. In addition, once the projections forming the cutting edges of the milling tool are dull, the entire milling tool is typically discarded.

It would be desirable to provide a reaming tool fabricated from heat treated machined metal components to provide greater cutting accuracy, and at lower manufacturing costs than conventional surgical cutters. In this regard it would be desirable to form the cutters of a hardened cutting material to provide superior cutting edges. In addition, it would be desirable to provide a reaming tool with replaceable cutting edges, so that once the cutting edges become dull, they can be removed, resharpened, and replaced, for improved economy of use and maintenance. The present invention meets these needs.

SUMMARY OF THE INVENTION

Briefly, and in general terms, the present invention provides for an improved reaming tool that is fabricated from machined metal components to provide greater cutting accuracy, and at lower manufacturing costs than conventional cutters. The reaming tool has a multiplicity of cutters that can be formed of heat treated tool steel, to provide superior cutting edges. In addition, once the individual cutters become dull, they can readily be removed, replaced, and can even be resharpened and used again, for improved economy of use and maintenance.

The present invention accordingly provides for a rotary surgical reamer for removing bone and tissue from a joint to facilitate the installation of a prosthetic device. The rotary surgical reamer comprises a hollow reamer body, the hollow reamer body having a base portion, a wall with a surface defining a central cavity and a plurality of spaced apart apertures through the wall at a plurality of spaced apart locations on the wall defining cutting sites. Means are provided for connecting the hollow reamer body to a source of rotary power, and a plurality of teeth are removably disposed in the apertures. Each of the teeth have a tooth body having a base portion and a raised cutting edge, and the tooth body includes means for holding the tooth in a fixed position at one of the cutting sites. The tooth body also has a surface defining a passageway communicating between the external surface of the wall and the central cavity for passage of removed bone and tissue through the wall into the central cavity. In a currently preferred embodiment, the tooth body includes a flange for spacing the cutting edge a desired distance beyond the external surface of the wall of the reamer body. In one presently preferred embodiment, the teeth have a generally tubular shape.

The hollow reamer body preferably has a shape with a central axis of rotation about which perpendicular cross-sectional cutting patterns are generated during rotation of the hollow reamer body, allowing the hollow reamer body to be rotated without wobbling. In one presently preferred embodiment, the external surface of the hollow reamer body has a three-dimensional contour that is generally hemispherical, although the hollow reamer body may also have a three-dimensional contour selected from the group consisting of generally spherical, oblate spheroid, generally cylindrical, generally polygonal, or combinations thereof. Means for connecting the hollow reamer body to a source of rotary power is carried on the base portion of the hollow reamer body.

In one presently preferred embodiment, the external surface of the hollow reamer body has a three-dimensional contour having an apex, and the plurality of cutting sites are spaced apart in an arcuate array extending from a site adjacent the apex toward the base portion of the hollow reamer body, forming a helical pattern. In another presently preferred embodiment, the cutting sites are arranged in a plurality of arcs extending from a site adjacent to an apex of the hollow reamer body to the base portion.

In another preferred aspect of the invention, the rotary surgical reamer includes closure means adapted to be secured to the base portion of the hollow reamer body. In a presently preferred embodiment, the closure means comprises a base plate removably disposed on the base portion of the hollow reamer body and means for securing the base plate to the base portion of the hollow reamer body for closure of the central cavity of the hollow reamer body. The internal surface of the central cavity preferably defines at least one inner annular groove, and the means for securing the base plate to the base portion of the hollow reamer body comprises a retaining spring having first and second ends and having a relaxed bent configuration and a compressed configuration in which the ends of the retaining spring can be extended into the inner annular groove of the base portion of the hollow reamer body.

A drive shaft is also provided for transmitting torque for rotation of the hollow reamer body, the retaining spring having a surface defining a central aperture for receiving the drive shaft, and the base plate having a surface defining a central aperture for receiving the drive shaft for transmitting torque for rotation of the hollow reamer body. The drive shaft has a terminal end that is press fit into the central aperture in the base plate, and the terminal end of the drive shaft has a transverse aperture in the shaft, and a retaining pin adapted to be received in the transverse aperture that when received in the transverse aperture extends above the surface of the shaft, for securing the drive shaft to the base plate.

In one currently preferred embodiment, the means for securing the base plate to the base portion of the hollow reamer body includes a retaining spring having a relaxed bent configuration and a compressed, substantially flat configuration in which the terminal ends of the retaining spring can be extended into the inner annular groove of the base portion of the hollow reamer body. The retaining spring also preferably has a central aperture with a notch to allow the drive shaft to pass through the retaining spring.

A tubular collar is provided for securing the retaining spring in the compressed configuration. The tubular collar is provided with a keyway for receiving a retaining pin inserted in the shaft, such that the tubular collar can be placed over the shaft and pressed against the retaining spring and rotated to lock the pin in the collar in a position pressing against the retaining spring, so that the retaining spring is locked in the flattened configuration.

In an alternate preferred embodiment, the hollow reamer body comprises a hollow can having a base portion, a wall with a top surface and an internal surface defining a central cavity and a plurality of spaced apart cutting sites on the wall. The hollow can has a central axis of rotation about which perpendicular cross-section cutting patterns are generated upon rotation of the hollow can, allowing the hollow can to be rotated without wobbling. The base portion of the hollow can also preferably includes means for connecting the hollow can to a source of rotary power. In this embodiment, the plurality of cutting sites comprises a site located adjacent to the axis of the can, with a plurality of sites arrayed in a plurality of arcs extending on the top surface of the can from the axis of the can to the edge of the top surface.

These and other aspects and advantages of the invention will become apparent from the following detailed description and the accompanying drawings, which illustrate by way of example the features of the invention.

BRIEF DESCRIPTION OF THE DRAWINGS

FIG. 7 is a schematic diagram of a pattern of placement of the cutters of the hollow dome reamer;

FIG. 8 is a schematic diagram of an alternate pattern of placement of the cutters of the hollow dome reamer;

FIG. 19 is a plan view of a ring lock spring adapted to be received on the annular groove of the drive shaft;

FIG. 20 is a partial view of a hollow drive rod adapted to fit over the drive shaft and ring lock spring;

FIG. 21 is a sectional view of an alternate embodiment of a hollow reamer body of the hollow dome reamer of the invention having a shape for use as a glenoid reamer;

FIG. 22 is a sectional view of another alternate embodiment of a hollow reamer body of the hollow dome reamer of the invention having an inverted curved shape for use as a femur or glenoid reamer;

FIG. 23 is a sectional view of another alternate embodiment of a hollow reamer body of the hollow dome reamer of the invention having a tiered shape with flattened shoulders for use as a patella recessing tool; and FIG. 24 is a top plan view of the hollow reamer body of FIG. 23 showing the pattern of the cutting teeth.

DETAILED DESCRIPTION OF THE PREFERRED EMBODIMENTS

Figure 1:
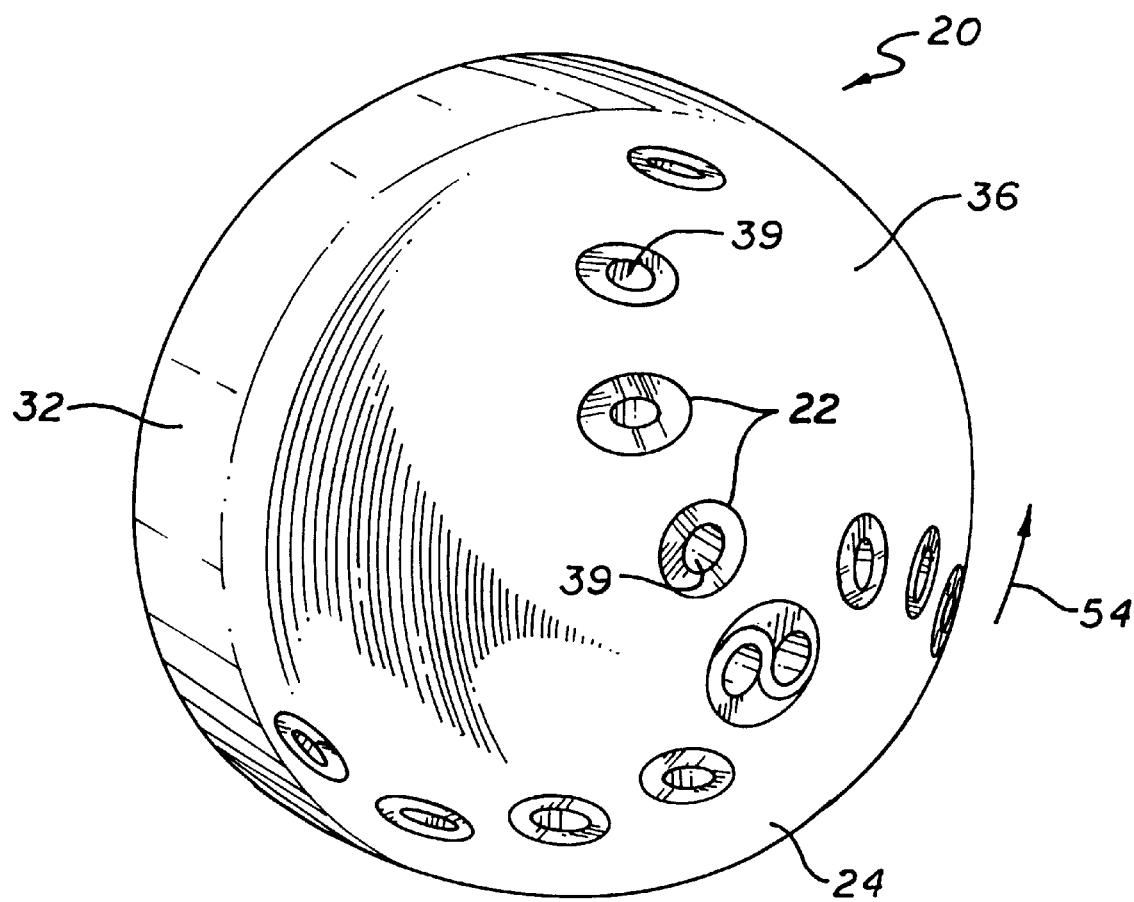
FIG. 1 is a perspective view of an hollow dome reamer with removable, replaceable cutters according to the present invention.
Figure 2:
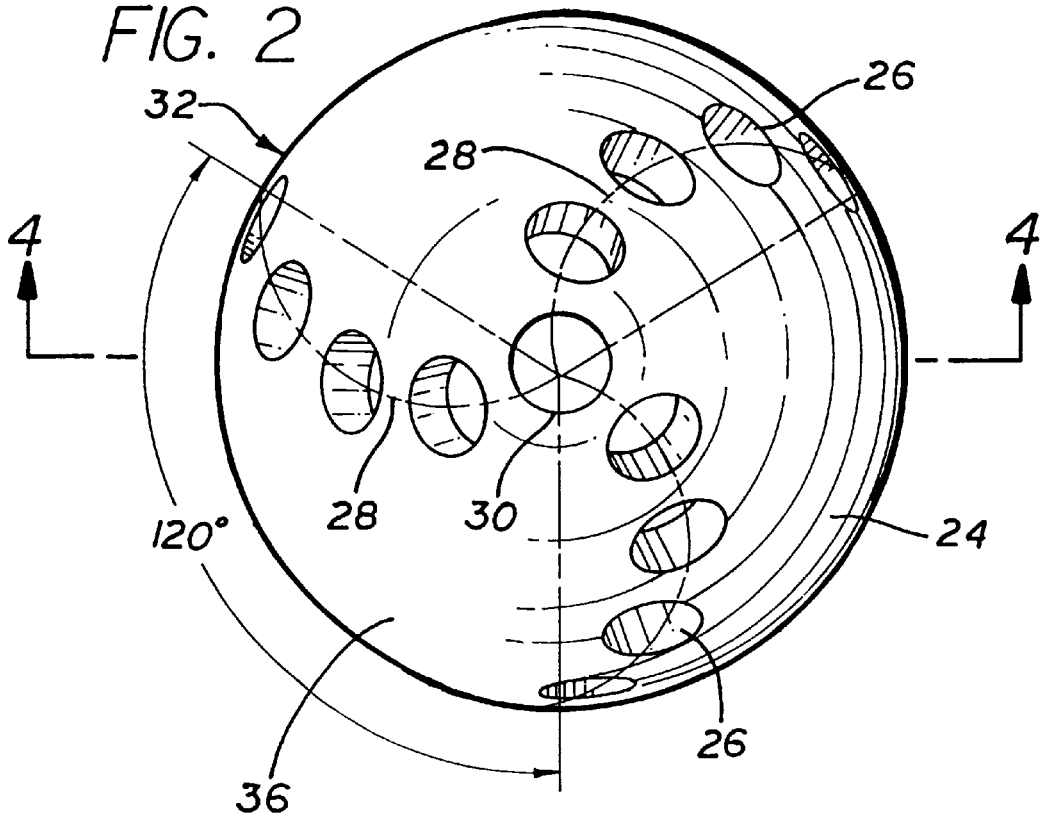
FIG. 2 is a top plan view of the hollow dome reamer of FIG. 1.
Figure 3:
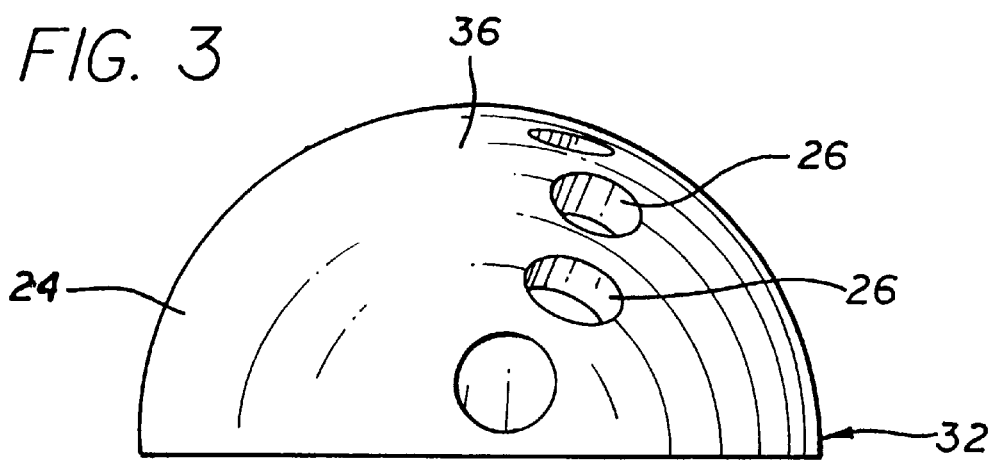
FIG. 3 is a side elevational view of the hollow dome reamer of FIG. 1.

During surgery for preparation of a joint for installation of a joint prosthesis, it has become important to capture and preserve the tissue and debris removed from a joint for later use. However, conventional surgical tools with hollow cutting heads that are typically used for this type of surgery commonly have cup-shaped cutting edge projections that are relatively thin, become dull relatively rapidly during use, and are not readily sharpened or replaced, so that once the cutting edges of the surgical tool become dull, the surgical tool is useless.

As is illustrated in the drawings, the invention is accordingly embodied in a hollow dome reamer that provides greater cutting accuracy, with removable teeth having superior cutting edges. The removable teeth can readily be replaced, and resharpened for repeated usage. Referring to FIGS. 1 through 11, the hollow dome reamer 20 is preferably a rotary surgical reamer having a plurality of inserted modular teeth 22 or cutters that are removably disposed in a hollow reamer body or dome 24 having a plurality of apertures 26 formed therein spaced apart at various locations around the dome. In one presently preferred embodiment, the dome has a hemispherical shape, although other three dimensional geometrical shapes may also be desirable and suitable for different applications, and in general the dome may be shaped to be generally spherical, an oblate spheroid, generally cylindrical, generally polygonal, and combinations thereof. The dome is also advantageously shaped to have a central axis of rotation about which perpendicular cross-sectional cutting patterns are generated during rotation of the hollow reamer body, allowing the hollow reamer body to be rotated without wobbling. In a presently preferred embodiment, the teeth are tubular, and the apertures are correspondingly cylindrical to accept the tubular teeth, but other geometrical shapes of the teeth and the apertures may also be suitable. The apertures of the dome and the tubular teeth are currently preferably dimensioned so that the tubular teeth can be press fit into the apertures in the dome; although threading the tubular teeth and the apertures to have corresponding threads to allow the tubular teeth to be threadedly secured in the dome, and other similar ways of securing the tubular teeth in the cylindrical apertures of the dome may also be suitable.

As can best be seen in FIGS. 2, 3, 5, 7 and 8, the apertures are preferably arranged in a plurality of arcs 28 extending from an apex 30 of the dome to the base portion 32 of the dome. In one presently preferred embodiment illustrated in FIGS. 1 to 5 and 7, a tubular cutter or tooth is provided in an apex aperture located off-center at the apex of the dome, with tubular teeth being provided in a series of three equally spaced arcs of spaced apart apertures, each of the arcs commencing at the center of the apex aperture and extending to the periphery of the base portion, with the apertures in the arcs being regularly spaced apart at pre-determined distances along the arcs. In this embodiment, there are currently preferably three equally spaced arcs, with three regularly spaced apertures in each arc, but greater numbers of arcs may also be suitable.

In an alternative preferred embodiment illustrated in FIG. 8, a tubular tooth is provided in an apex aperture located adjacent to the apex of the dome, with tubular teeth being provided in an arcuate, generally helical path of spaced apart apertures, the arc commencing generally at the apex of the dome and extending to the periphery of the base portion. The apertures in the helical arc are preferably spaced apart at pre-determined distances along the arcs such that all of the apertures fall on a spiral line extending from the apex aperture of the dome to the periphery of the base portion.

Figure 4:
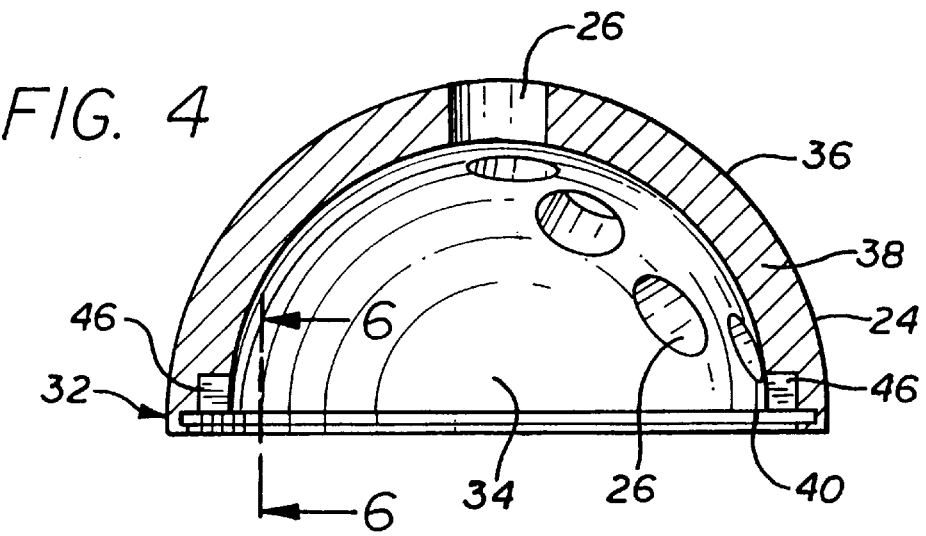
FIG. 4 is a cross-sectional view of the hollow dome reamer taken along line 4—4 of FIG. 2.
Figure 5:
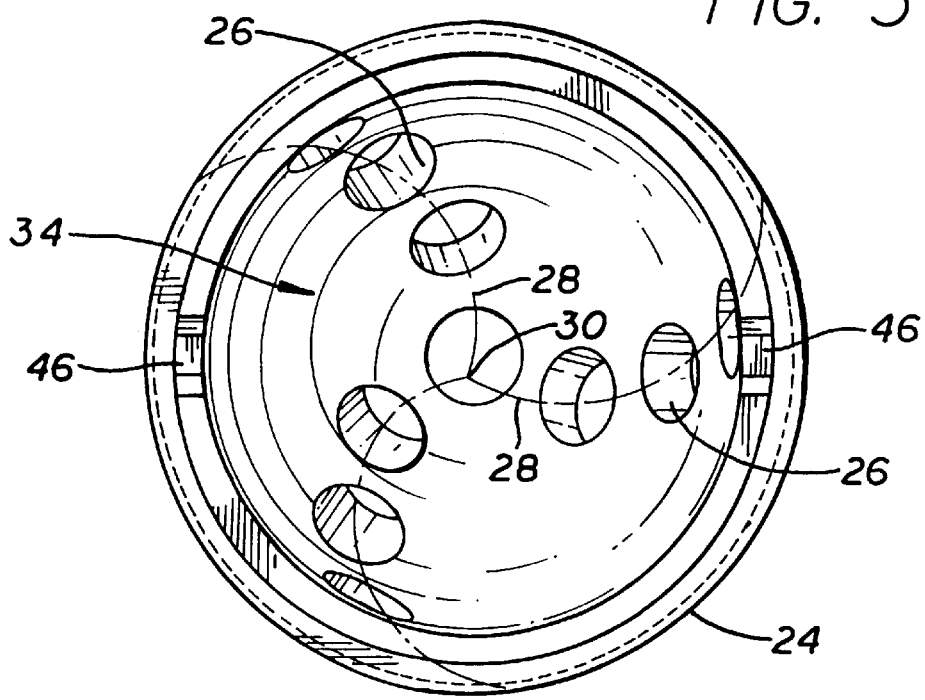
FIG. 5 is a bottom plan view of the hollow dome reamer of FIG. 1.
Figure 6:
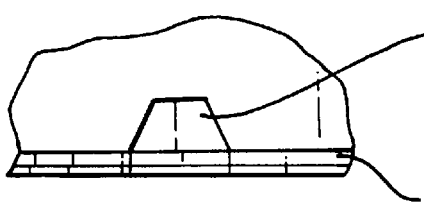
FIG. 6 is a side elevational view of a portion of the hollow dome reamer taken along line 6—6 of FIG. 4.

Referring to FIGS. 4 and 5, the dome has an inner central cavity 34 or chamber, a hemispherical external surface 36, and an outer wall 38 having a thickness that is sufficient to provide adequate support for a plurality of the tubular teeth disposed in the apertures of the dome. Each tubular tooth preferably also has an interior passageway 39, so that when the teeth are inserted in the apertures of the dome, the hollow tubular teeth provide communication between the external and internal areas of the dome through the wall. As explained above, while the teeth are currently preferably tubular, and the apertures are cylindrical, other cross-sectional shapes of the teeth and apertures may also be suitable as long as an interior passageway is provided in the teeth, and the teeth can be removably disposed in the apertures of the dome.

The base portion of the dome preferably has at least one inner annular groove 40 that can be seen in FIG. 4, for receiving the terminal ends 42 of a retaining spring 44 of the base plate, and a plurality of notches 46 adapted to receive corresponding key flanges 48 of the base plate, described below. In one presently preferred embodiment, the base portion of the dome has two diametrically opposed notches adapted to receive corresponding key flanges of the base plate. The dome is currently preferably formed from metal, such as steel, such as stainless steel or tool steel for example, titanium alloy, aluminum, aluminum alloy, nitinol, and molybdenum, although the dome can be made of other suitable materials, such as ceramic or plastic, for example.

Figure 9:
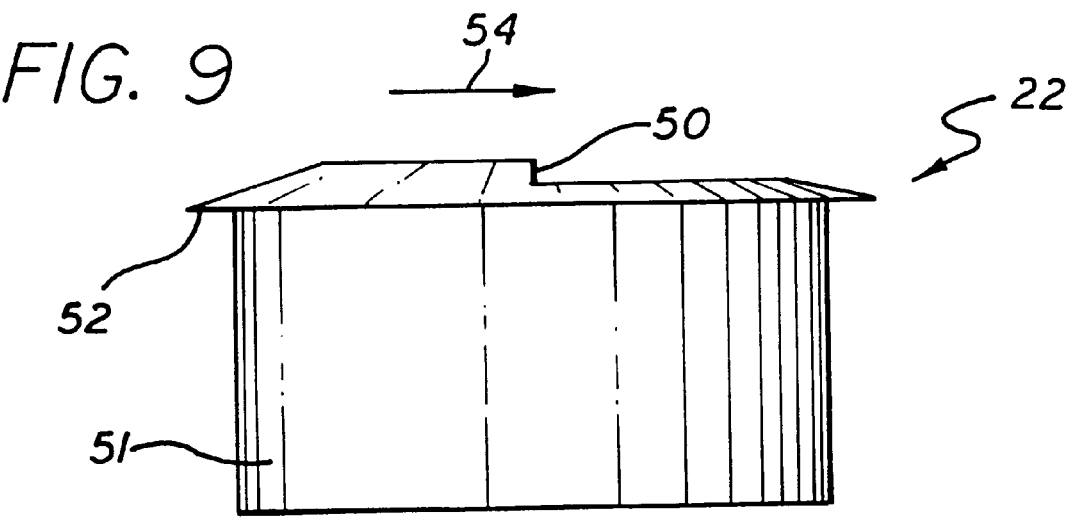
FIG. 9 is a side elevational view of a cutter of the hollow dome reamer of FIG. 1 according to the invention.
Figure 10:
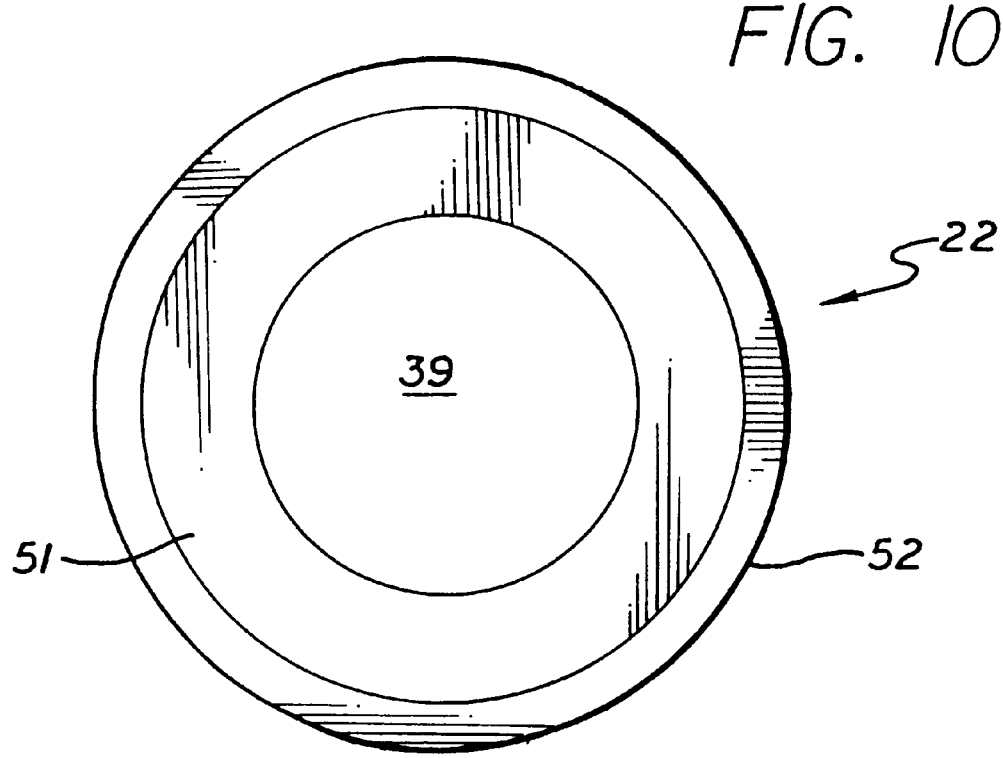
FIG. 10 is a bottom plan view of the cutter of FIG. 9.
Figure 11:
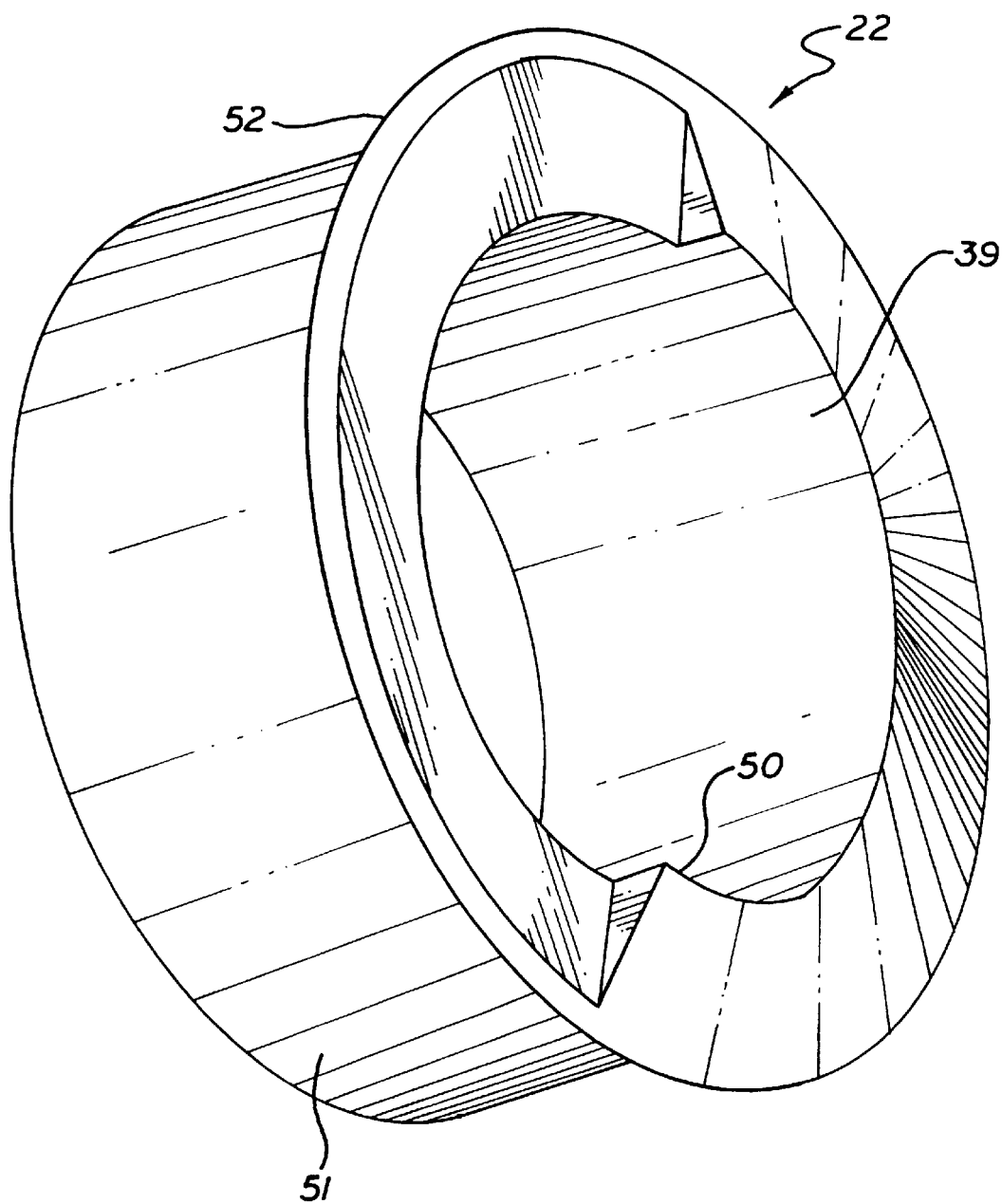
FIG. 11 is a perspective view of the cutter of FIG. 9.

As can best be seen in FIGS. 9 and 11, the tubular teeth each have a raised cutting edge 50, a tubular base portion 51, and a flange 52 or shoulder that is aligned with the hemispherical external surface of the dome to position the cutting edges of the teeth at a specific desired distance above or beyond the hemispherical external surface of the dome. The teeth are currently preferably fabricated of heat treated tool steel, although the teeth can also be formed from other suitable materials, such as stainless steel, ceramic, plastic, titanium alloy, aluminum alloy, nitinol, and molybdenum. Each cylindrical, tubular tooth insert is preferably formed by cutting a tube formed of tool steel into segments, and grinding down a portion of one end of a segment to form the flange or shoulder, and leaving the raised portion of the end of the segment as the cutting edge. The cylindrical, tubular tooth insert is then press fit in an aperture of the dome, oriented so that the flange is flush with the external surface of the dome and facing in a direction of rotation 54 of the dome, so that when the dome is rotated in the specified direction, the raised circular cutting edge section will perform the cutting of bone and other tissue, which will then be extruded through the central hole or passageway 39 in the tooth and into the central cavity of the dome.

Figure 12:
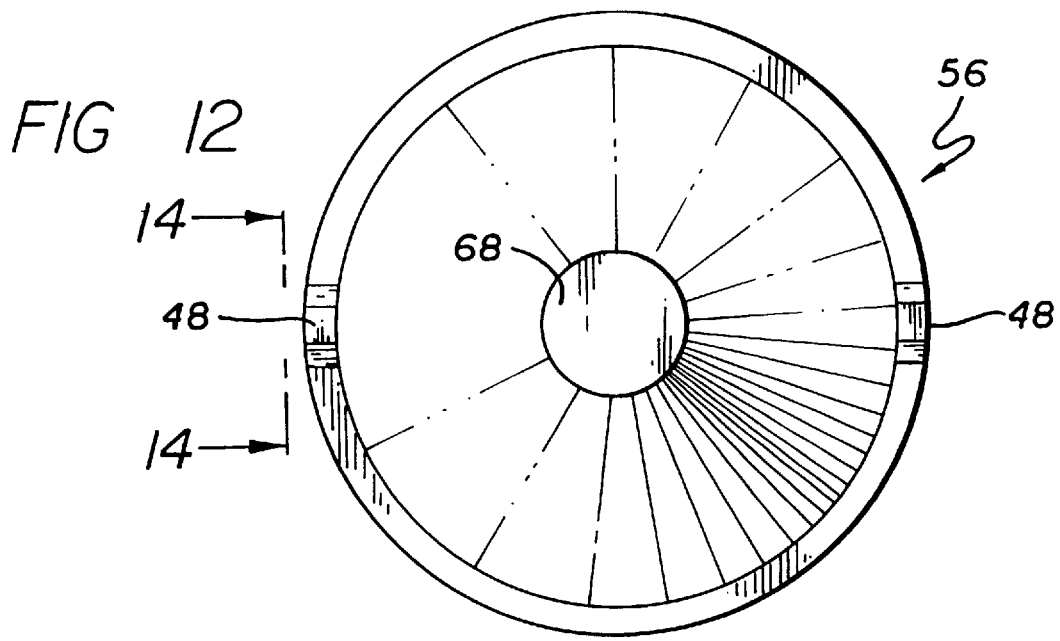
FIG. 12 is a bottom plan view of the base plate and drive shaft of the hollow dome reamer of FIG. 1 according to the invention.
Figure 13:
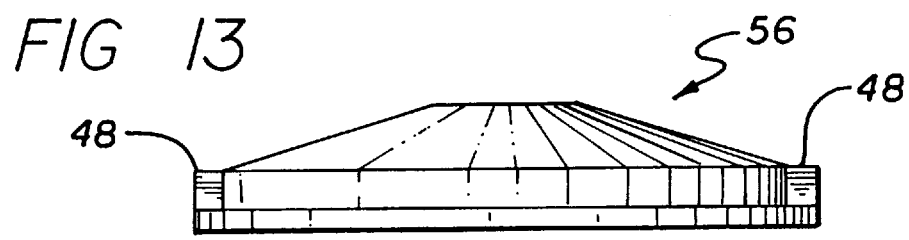
FIG. 13 is a side elevational view of the base plate of FIG. 12, shown without the drive shaft, for the sake of simplicity.
Figure 14:
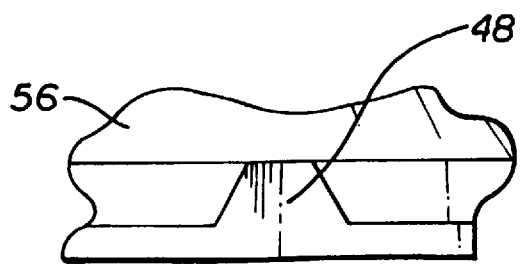
FIG. 14 is a side elevational view of a portion of the base plate taken along line 14—14 of FIG. 12, showing a key flange corresponding to the notches in the dome.

With reference to FIGS. 12 to 14, the hollow dome reamer also includes a circular base plate 56 with a plurality of key flanges 48 adapted to be received in the corresponding notches 46 of the base portion of the dome. The base plate is removably disposed on the base portion of the dome, and achieves closure of the central cavity of the dome. In a currently preferred embodiment, the circular base plate has a pair of diametrically opposed key flanges, and means 58 for securing the base plate to the base portion of the dome.

Figure 17:
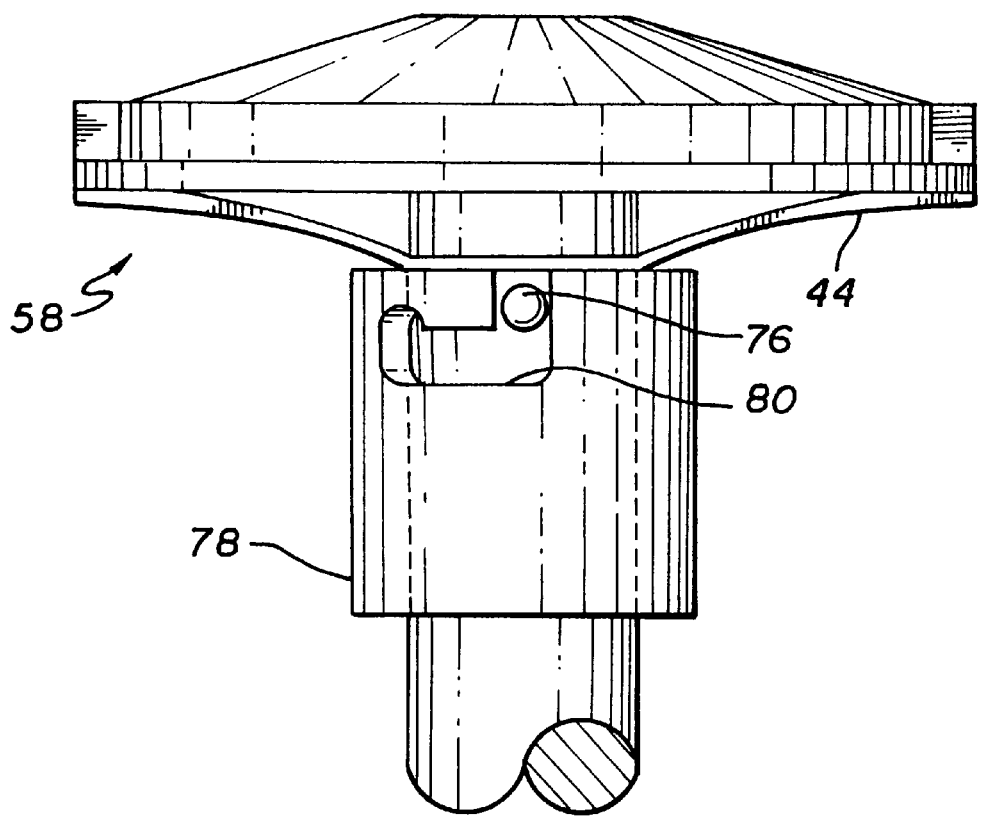
FIG. 17 is another side elevational view of the base plate and drive shaft of the hollow dome reamer of FIG. 1 showing the placement of a retaining spring over the drive shaft and retaining pin according to the invention.
Figure 18:
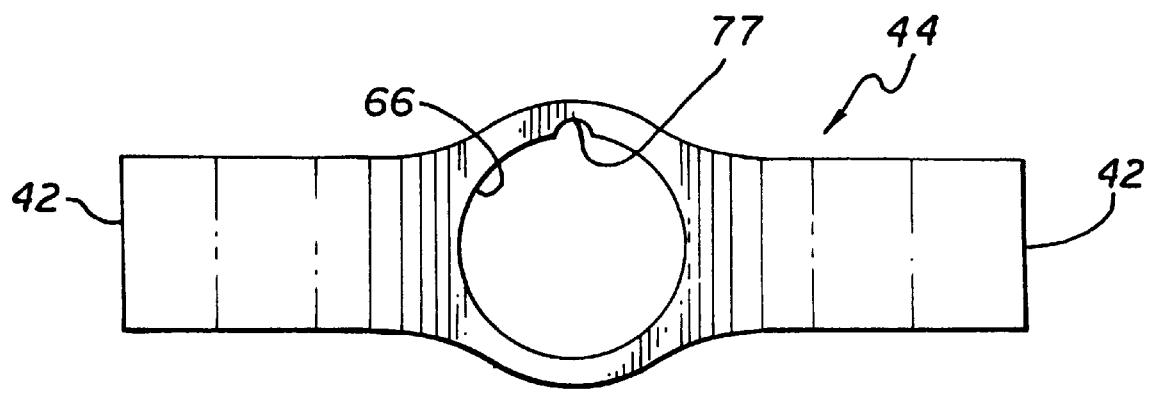
FIG. 18 is a plan view of the retaining spring of FIG. 17 according to the invention.

In a currently preferred embodiment, the means for securing the base plate to the base portion of the dome comprises a leaf spring retaining spring 44 shown in FIGS. 17 and 18 that has a compressed, considerably flattened configuration in which the terminal ends of the retaining spring can be extended into the inner annular groove 40 of the base portion of the dome, and a relaxed, slightly bent configuration illustrated in FIG. 17 in which the terminal ends of the retaining spring do not extend into the inner annular groove of the base portion of the dome. The retaining spring preferably has a central aperture 66 to allow passage of a drive shaft, shown in FIGS. 15 and 17, through the retaining spring, and the circular base plate also has a central aperture 68 for receiving the drive shaft. The drive shaft 70 is provided for transmitting torque for rotation of the dome. The drive shaft has a terminal end 72 that is press fit into the aperture 68 in the base plate. The terminal end 72 of the shaft also has an aperture 74 for receiving a retaining pin 76 that, when received in the aperture of the terminal end of the drive shaft, extends above the surface of the drive shaft, for securing the drive shaft to the base plate. The retaining spring central aperture also includes a notch 77 to allow the retaining spring to slide over the retaining pin 76 of the drive shaft.

Figure 16:
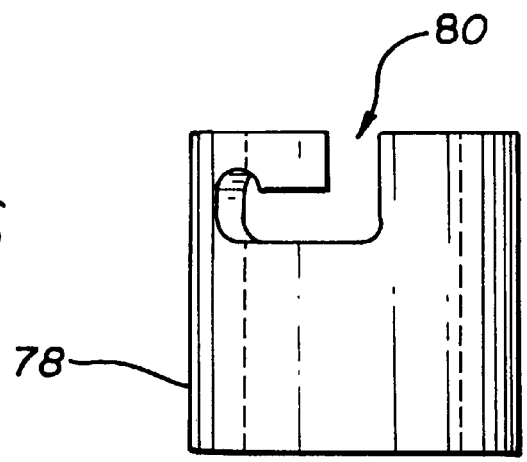
FIG. 16 is a side elevational view of a retaining collar for compressing the retaining spring to engage the inner annular groove of the dome, according to the invention.

Referring to FIGS. 16 and 17, a tubular collar 78 having a keyway 80 for receiving the pin of the shaft is also provided that fits over the drive shaft. The collar can be pressed against the retaining spring to flatten it, and then rotated to lock the pin in the keyway of the collar, so that the retaining is locked in a flattened configuration.

Figure 15:
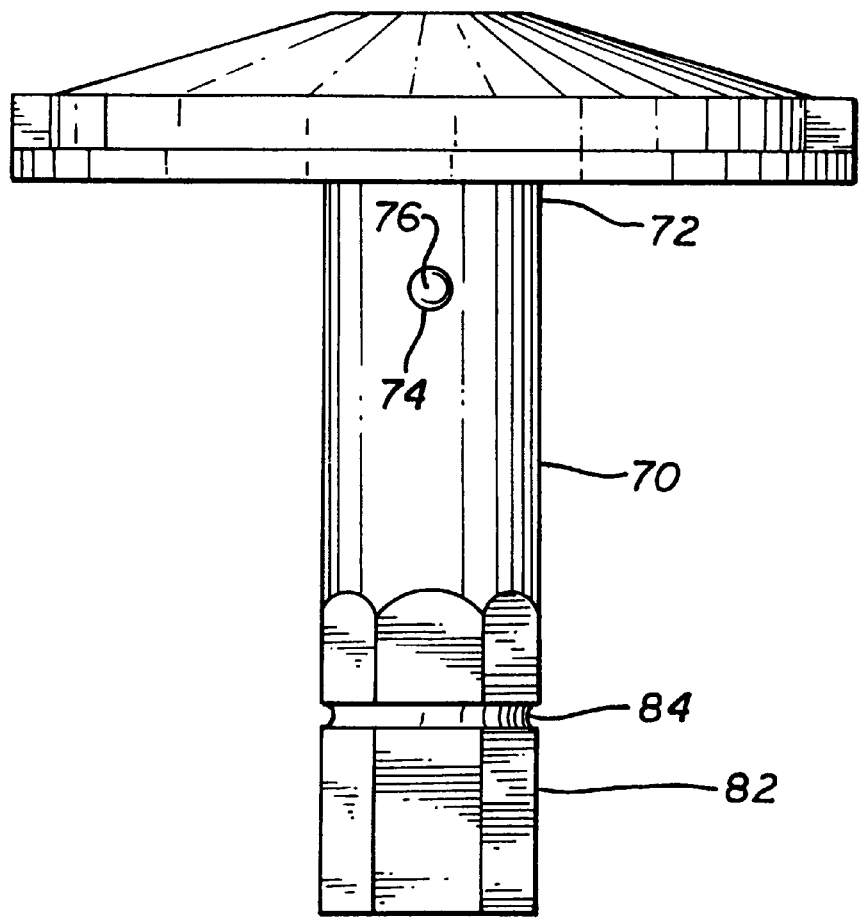
FIG. 15 is another side elevational view of the base plate and drive shaft of the hollow dome reamer of FIG. 1 showing the placement of a retaining pin according to the invention.

With reference to FIGS. 15 and 19, the proximal end 82 of the drive shaft also preferably has an annular groove 84 for receiving an annular spring lock 86 shown in FIG. 19. The spring lock comprises a main loop 88 that is received in the annular groove of the drive shaft, an arm 90 extending generally perpendicular to the curve of the loop, and a ball tip 92 at the distal end of the arm. Referring to FIG. 20, the arm and ball tip of the spring lock are adapted to be received in a slot 94 of a slotted collar 96 of a hollow drive rod 98, adapted to be connected to a source of rotary drive power, such as an electric drill motor.

FIG. 21 illustrates a first variant of the shape of the hollow reamer body illustrated in FIGS. 1-8, adapted for use as a glenoid reamer. In this variant, the shape of the external cutting surface of the hollow reamer body can be generally convex, but not necessarily hemispherical, and is similar in many respects to the embodiment illustrated in FIGS. 1-8, so that elements of the first variant that are similar to those of the first embodiment described above are described with similar reference numbers. The convex hollow dome glenoid reamer 120 preferably has a plurality of inserted modular teeth 122 that are removably disposed in the hollow reamer body or dome 124 having a plurality of apertures 126 formed therein spaced apart at various locations around the dome. The dome of the glenoid reamer is shaped to have a central axis of rotation about which perpendicular cross-sectional cutting patterns are generated during rotation of the hollow reamer body, allowing the hollow reamer body to be rotated without wobbling.

As was illustrated in FIGS. 1-5 and 7-8 in connection with the first embodiment, in the glenoid variant of the hollow dome reamer, the apertures are preferably arranged in a plurality of arcs extending from an apex of the dome to the base of the dome. Alternatively, a tubular tooth can be provided in an apex aperture located adjacent to the apex of the dome, with tubular teeth being provided in an arcuate, generally helical path of spaced apart apertures, the arc commencing generally at the apex of the dome and extending to the periphery of the base portion.

The hollow reamer body or dome has an inner central cavity 134 or chamber, an external surface 136, and an outer wall 138 having a thickness that is sufficient to provide adequate support for a plurality of the tubular teeth disposed in the apertures of the dome. The cutting teeth are as described hereinabove. As explained above, while the teeth are currently preferably tubular, and the apertures are cylindrical, other cross-sectional shapes of the teeth and apertures may also be suitable as long as an interior passageway is provided in the teeth, and the teeth can be removably disposed in the apertures of the dome. The base portion 132 of the dome preferably has an integral base plate 140 having an aperture for receiving a drive shaft for supplying rotary power to the reamer.

In another presently preferred variant of the hollow reamer body illustrated in FIG. 22, the shape of the hollow reamer body is adapted for use as a femur or glenoid reamer. In this second variant, the shape of the external cutting surface of the hollow reamer body can be generally concave, but not necessarily hemispherical, and is similar in many respects to the embodiment illustrated in FIG. 21, so that elements ofthis second variant that are similar to those described above are described with similar reference numbers. The hollow dome glenoid reamer 220 preferably has a plurality of inserted teeth 222 that are removably disposed in the hollow reamer body or dome 224 having a plurality of apertures 226 formed therein spaced apart at various locations around the dome. The dome of the concave femur or glenoid reamer is shaped to have a central axis of rotation about which perpendicular cross-sectional cutting patterns are generated during rotation of the hollow reamer body, allowing the hollow reamer body to be rotated without wobbling.

As was illustrated in FIGS. 1-5 and 7-8 in connection with the first embodiment, in the glenoid variant of the hollow dome reamer, the apertures are preferably arranged in a plurality of arcs extending from an apex of the dome to the base of the dome. Alternatively, a tubular tooth can be provided in an apex aperture located adjacent to the apex of the dome, with tubular teeth being provided in an arcuate, generally helical path of spaced apart apertures, the arc commencing generally at the apex of the dome and extending to the periphery of the base portion.

The hollow reamer body or dome has an inner central cavity 234 or chamber, an external surface 236, and an outer wall 238 having a thickness that is sufficient to provide adequate support for a plurality of the tubular teeth disposed in the apertures of the dome. The cutting teeth are as described hereinabove. As explained above, while the teeth are currently preferably tubular, and the apertures are cylindrical, other cross-sectional shapes of the teeth and apertures may also be suitable as long as an interior passageway is provided in the teeth, and the teeth can be removably disposed in the apertures of the dome. The base portion 232 of the dome preferably has an integral base plate 240 having an aperture for receiving a drive shaft for supplying rotary power to the reamer.

In another presently preferred variant of the hollow reamer body illustrated in FIGS. 23 and 24, the shape of the hollow reamer body is adapted for use as a patella recessing tool. In this third variant, the shape of the external cutting surface of the hollow reamer body can be generally tiered to have two or three tiers for example. Referring to the specific embodiment shown in FIGS. 23 and 24, the patella recessing reamer provides a generally flat raised first inner tier 316, and a generally flat lower second tier 318. This embodiment is similar in many respects to the embodiments illustrated in FIGS. 21 and 22, so that elements of this third variant that are similar to those described above are described with similar reference numbers. The hollow dome patella recessing reamer 320 preferably has a plurality of inserted teeth 322 that are removably disposed in the hollow reamer body or dome 324 having a plurality of apertures 326 formed therein spaced apart at various locations around the dome. The dome of the tiered patella recessing reamer is shaped to have a central axis of rotation about which perpendicular cross-sectional cutting patterns are generated during rotation of the hollow reamer body, allowing the hollow reamer body to be rotated without wobbling.

As is shown in FIG. 24, in the patella recessing variant of the hollow dome reamer, the apertures are preferably arranged in a plurality of arcs extending from an apex of the dome to the base of the dome. Alternatively, a tubular tooth can be provided in an apex aperture located adjacent to the apex of the dome, with tubular teeth being provided in an arcuate, generally helical path of spaced apart apertures, the arc commencing generally at the apex of the dome and extending to the periphery of the base portion.

The hollow reamer body or dome has an inner central cavity 334 or chamber, an external surface 336, and an outer wall 338 having a thickness that is sufficient to provide adequate support for a plurality of the tubular teeth disposed in the apertures of the dome. The cutting teeth are as described hereinabove. As explained above, while the teeth are currently preferably tubular, and the apertures are cylindrical, other cross-sectional shapes of the teeth and apertures may also be suitable as long as an interior passageway is provided in the teeth, and the teeth can be removably disposed in the apertures of the dome. The base portion 332 of the dome preferably has an integral base plate 340 having an aperture for receiving a drive shaft for supplying rotary power to the reamer.

It has thus been demonstrated that the present invention provides for a reaming tool that provides greater cutting accuracy, with tubular teeth superior cutting edges that can readily be removed, replaced, and resharpened for repeated usage. The tubular teeth can be simply and inexpensively manufactured from hardened tool steel. The present invention thus provides for an improved hollow dome reamer providing for improved economy of use and maintenance, and at lower manufacturing costs than other conventional hollow dome reamers.

It should be recognized that other patterns of the teeth on the dome may also be suitable, such as a random scattering of locations of the teeth on the dome, or a symmetrical balancing of locations of the teeth on the dome so that forces exerted on the dome would be generally balanced. Other suitable closure means also may alternatively be provided, such as by simply providing the circular base plate with peripheral threads adapted to interfit with corresponding threads on the inner base portion of the dome, with the direction of the threading being such that the base plate can be secured to the dome by rotating the base plate in the direction of rotation of the dome.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A rotary surgical reamer for removing bone and tissue from a joint to facilitate the installation of a prosthetic device, the rotary surgical reamer comprising:

a hollow reamer body, said hollow reamer body having a base portion, a wall with a surface defining a central cavity and a plurality of spaced apart apertures through said wall at a plurality of spaced apart locations on said wall defining cutting sites;

means for connecting said hollow reamer body to a source of rotary power; and a plurality of teeth removably disposed in said apertures, each of said teeth having a tooth body having a base portion and a raised cutting edge, said tooth body providing means for holding each said tooth in a fixed position at one of said cutting sites, and said tooth body having a surface defining a passageway communicating between the external surface of said wall and said central cavity for passage of removed bone and tissue through said wall into said central cavity.

2. The rotary surgical reamer of claim 1, wherein tooth body further comprises a flange for spacing the cutting edge a desired distance beyond the external surface of said wall of said reamer body.

3. The rotary surgical reamer of claim 1, wherein said hollow reamer body has a shape with a central axis of rotation about which perpendicular cross-sectional cutting patterns are generated during rotation of the hollow reamer body, allowing the hollow reamer body to be rotated without wobbling.

4. The rotary surgical reamer of claim 1, wherein said external surface of said hollow reamer body has a three-dimensional contour that is generally hemispherical.

5. The rotary surgical reamer of claim 1, wherein said external surface of said hollow reamer body has a three-dimensional contour selected from the group consisting of generally spherical, oblate spheroid, generally cylindrical, generally polygonal, and combinations thereof.

6. The rotary surgical reamer of claim 1, wherein said teeth have a generally tubular shape.

7. The rotary surgical reamer of claim 1, wherein said means for connecting said hollow reamer body to a source of rotary power is carried on said base portion of said hollow reamer body.

8. The rotary surgical reamer of claim 1, wherein said external surface of said hollow reamer body has a three-dimensional contour having an apex, and the plurality of cutting sites being spaced apart in an arcuate array extending from a site adjacent the apex toward the base portion of the hollow reamer body, forming a helical pattern.

9. The rotary surgical reamer of claim 1, wherein said cutting sites are arranged in a plurality of arcs extending from a site adjacent to an apex of said hollow reamer body to said base portion.

10. The rotary surgical reamer of claim 1, wherein said teeth are made of a material selected from the group consisting of stainless steel, tool steel, ceramic, plastic, titanium alloy, aluminum alloy, nitinol, and molybdenum.

11. The rotary surgical reamer of claim 1, wherein said hollow reamer body is made of a material selected from the group consisting of stainless steel, tool steel, ceramic, plastic, titanium alloy, aluminum alloy, nitinol, and molybdenum.

12. The rotary surgical reamer of claim 1, wherein said teeth are positioned so that the cutting edges face in a direction of rotation of the hollow reamer body.

13. The rotary surgical reamer of claim 1, further comprising closure means adapted to be secured to said base portion of said hollow reamer body.

14. The rotary surgical reamer of claim 13, wherein said closure means comprises a base plate removably disposed on said base portion of said hollow reamer body and means for securing said base plate to said base portion of said dome for closure of said central cavity of said dome.

15. The rotary surgical reamer of claim 14, wherein said internal surface of said central cavity defines at least one inner annular groove, and said means for securing said base plate to said base portion of said dome comprises a retaining spring having first and second ends and having a relaxed bent configuration and a compressed configuration in which said ends of said retaining spring can be extended into said inner annular groove of said base portion of said hollow reamer body.

16. The rotary surgical reamer of claim 15, further comprising a drive shaft for transmitting torque for rotation of said hollow reamer body, said retaining spring having a surface defining a central aperture for receiving said drive shaft, and said base plate having a surface defining a central aperture for receiving said drive shaft for transmitting torque for rotation of said hollow reamer body.

17. The rotary surgical reamer of claim 16, wherein said drive shaft has a terminal end that is press fit into said central aperture in said base plate, and said terminal end of said drive shaft has a transverse aperture in said shaft, and a retaining pin adapted to be received in said transverse aperture that when received in said transverse aperture extends above the surface of said shaft, for securing said drive shaft to said base plate.

18. The rotary surgical reamer of claim 17, further comprising a tubular collar adapted to be received over said drive shaft and having a keyway for receiving said retaining pin, such that said tubular collar can be pressed against said retaining spring and rotated to lock said retaining pin in said tubular collar in a position pressing against said retaining spring, whereby said retaining spring is locked in a flattened configuration.

19. A rotary surgical reamer for removing bone and tissue from a joint to facilitate the installation of a prosthetic device, the rotary surgical reamer comprising:

a hollow, dome shaped body, said dome shaped body having a base portion, a wall with a surface defining a central cavity and a plurality of spaced apart cutting sites on said wall, the dome shaped body having a central axis of rotation about which perpendicular cross-section cutting patterns are generated upon rotation of said dome shaped body, allowing the dome shaped body to be rotated without wobbling;

means for connecting base portion of said dome shaped body to a source of rotary power; and a plurality of removable tubular cutters disposed at said cutting sites, each of said tubular cutters having a cutter body having a base portion and a raised cutting edge, said cutter body providing means for holding each said cutter in a fixed position at one of said cutting sites at a selected distance spaced from the external surface of said dome shaped body, and said cutter body having a surface defining a passageway communicating between the external surface of said wall and said central cavity for passage of removed bone and tissue through said wall into said central cavity.

20. The rotary surgical reamer of claim 19, wherein said plurality of cutting sites comprises an apex site located adjacent to the apex of the dome shaped body, with a plurality of sites arranged in an arc and spaced at predetermined distances extending from the apex of the dome shaped body to the base portion of the dome shaped body forming a helical pattern.

21. The rotary surgical reamer of claim 19, wherein the plurality of cutting sites comprises an apex site located adjacent to the apex of the dome, with a plurality of sites arrayed in a plurality of arcs commonly extending from the apex of the dome shaped body to the base portion of the dome shaped body.

22. The rotary surgical reamer of claim 19, wherein said tubular cutters are made of a material selected from the group consisting of stainless steel, tool steel, ceramic, plastic, titanium alloy, aluminum alloy, nitinol, and molybdenum.

23. The rotary surgical reamer of claim 19, wherein said hollow reamer body is made of a material selected from the group consisting of stainless steel, tool steel, ceramic, plastic, titanium alloy, aluminum alloy, nitinol, and molybdenum.

24. The rotary surgical reamer of claim 19, wherein said tubular cutters are oriented such that said cutting edge faces in a direction of rotation of the dome shaped body.

25. The rotary surgical reamer of claim 19, wherein said apertures are arranged in a plurality of arcs extending from an apex of said dome to said base portion of said dome.

26. The rotary surgical reamer of claim 19, further comprising closure means adapted to be secured to said base portion of said dome shaped body.

27. A rotary surgical reamer for removing bone and tissue from a joint to facilitate the installation of a prosthetic device, the rotary surgical reamer comprising:

a hollow can having a base portion, a wall with a top surface and an internal surface defining a central cavity and a plurality of spaced apart cutting sites on said wall, the hollow can having a central axis of rotation about which perpendicular cross-section cutting patterns are generated upon rotation of said dome shaped body, allowing the hollow can to be rotated without wobbling, and said base portion of said hollow can having means for connecting said hollow can to a source of rotary power; and a plurality of tubular cutters removably disposed at said cutting sites, each of said tubular cutters having a raised cutting edge, said tubular cutters being held in a fixed position spaced a selected distance from the external surface of said hollow can, and said tubular cutters having a surface defining a passageway communicating between the external surface of said wall and said central cavity for passage of removed bone and tissue through said wall into said central cavity.

28. The rotary surgical reamer of claim 27, wherein the plurality of cutting sites comprises a site located adjacent to the axis of the can, with a plurality of sites arrayed in a plurality of arcs extending on the top surface of the can from the axis of the can to the edge of the top surface.

29. The rotary surgical reamer of claim 27, wherein said tubular cutters are made of a material selected from the group consisting of stainless steel, tool steel, ceramic, plastic, titanium alloy, aluminum alloy, nitinol, and molybdenum.

30. The rotary surgical reamer of claim 27, wherein said hollow reamer body is made of a material selected from the group consisting of stainless steel, tool steel, ceramic, plastic, titanium alloy, aluminum alloy, nitinol, and molybdenum.

31. The rotary surgical reamer of claim 27, wherein said tubular cutters are oriented such that said cutting edge faces in a direction of rotation of the can.

* * * * *